(12) United States Patent
Yanagihara et al.

(10) Patent No.: US 7,316,903 B2
(45) Date of Patent: Jan. 8, 2008

(54) DETECTION OF NUCLEIC ACID SEQUENCE VARIATIONS USING PHASE MU TRANSPOSASE

(75) Inventors: Katsuhiko Yanagihara, Kyoto (JP); Kiyoshi Mizuuchi, Rockville, MD (US)

(73) Assignee: United States of America as represented by the Department of Health and Human Services, Washington, DC (US)

(*) Notice: Subject to any disclaimer, the term of this patent is extended or adjusted under 35 U.S.C. 154(b) by 390 days.

(21) Appl. No.: 10/809,688

(22) Filed: Mar. 26, 2004

(65) Prior Publication Data

US 2004/0191821 A1 Sep. 30, 2004

Related U.S. Application Data

(60) Provisional application No. 60/457,934, filed on Mar. 28, 2003.

(51) Int. Cl.
*C12Q 1/68* (2006.01)
*C12P 19/34* (2006.01)

(52) U.S. Cl. .......................... 435/6; 435/91.2
(58) Field of Classification Search .............. 435/6, 435/91.2
See application file for complete search history.

(56) References Cited

U.S. PATENT DOCUMENTS

| | | | |
|---|---|---|---|
| 4,716,105 A | 12/1987 | Mizuuchi et al. | |
| 4,946,773 A | 8/1990 | Maniatis et al. | |
| 5,698,400 A | 12/1997 | Cotton et al. | |
| 5,824,471 A | 10/1998 | Mashal et al. | |
| 5,851,770 A | 12/1998 | Babon et al. | |
| 5,925,545 A | 7/1999 | Reznikoff et al. | |
| 5,948,622 A | 9/1999 | Reznikoff et al. | |
| 5,958,692 A | 9/1999 | Cotton et al. | |
| 5,965,443 A | 10/1999 | Reznikoff et al. | |
| 6,191,268 B1 | 2/2001 | Liskay et al. | |
| 6,365,355 B1 | 4/2002 | McCutchen-Maloney | |
| 6,368,830 B1 * | 4/2002 | Lampe et al. | 435/69.1 |
| 6,391,557 B1 | 5/2002 | Yeung | |
| 6,437,109 B1 | 8/2002 | Reznikoff et al. | |
| 2005/0037011 A1 * | 2/2005 | Jones et al. | 424/155.1 |

OTHER PUBLICATIONS

Cotton, R.G.H., et al., "Reactivity of cytosine and thymine in single-base-pair mismatches with hydroxylamine and osmium tetroxide and its application to the study of mutations," *Proc. Natl. Acad. Sci. USA* 85: 4397-4401 (1988).

(Continued)

*Primary Examiner*—Kenneth R. Horlick
(74) *Attorney, Agent, or Firm*—Venable LLP; Ann S. Hobbs; Nancy J. Axelrod

(57) ABSTRACT

The present invention relates, e.g., to a method of detecting a mismatch in a double stranded nucleic acid target, comprising (a) contacting the target with (i) a Mu-end nucleic acid, and (ii) a phage Mu transposase, under conditions effective for the Mu-end nucleic acid to transpose into the target at about the site of a mismatch, if the target comprises a mismatch, and (b) detecting transposition of the Mu-end DNA into the target, wherein transposition of the Mu-end nucleic acid into the target at a predominant site indicates the presence of a mismatch at that site.

31 Claims, 6 Drawing Sheets

OTHER PUBLICATIONS

Mashal, R.D., et al., "Detection of mutations by cleavage of DNA heteroduplexes with bacteriophage resolvases," *Nature Genetics 9*: 177-183 (1995).

Myers, R.M., et al., "Detection of Single Base Substitutions by Ribonuclease Cleavage at Mismatches in RNA:DNA Duplexes," *SCIENCE 230*:1242-1246 (1985).

Orita, M., et al., "Detection of polymorphisms of human DNA by gel electrophoresis as single-strand conformation polymorphisms," *Proc. Natl. Acad. Sci. USA 86*: 2766-2770 (1989).

Savilahti, H., et al., "The phage Mu transpososome core: DNA requirements for assembly and function," *The EMBO Journal 14*: 4893-4903 (1995).

Yanagihara, K., et al., "Mismatch-targeted transposition of Mu: A new strategy to map genetic polymorphism," *Proc. Natl. Acad. Sci. USA 99*: 11317-11321 (2002).

Youil, R., et al., "Screening for mutations by enzyme mismatch cleavage with T4 endonuclease VII," *Proc. Natl. Acad. Sci. USA 92*: 87-91. (1995).

\* cited by examiner

FIG. 1A-c

SEQUENCE LISTING

<160> NUMBER OF SEQ ID NOS: 8

<210> SEQ ID NO 1
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
tcggatgaag cggcgcacga aaaacgcgaa agcgtttcac gataaatgcg aaaaca    56

<210> SEQ ID NO 2
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2
tgttttcgca tttatcgtga aacgctttcg cgttttttcgt gcgccgcttc a    51

<210> SEQ ID NO 3
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cgttcattag cacaatcaca gaagactaga atacaaccgc acataagatc agaagttaac    60
tagcactagt acttgc                                                   76

<210> SEQ ID NO 4
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gcaagtacta gtgctagtta acttctgatc ttatgtgcgg ttgtattcta gtcttctgtg    60
attgtgctaa tgaacg                                                   76

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 5
tggtaatagg acatctccaa g                                             21

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 6
accttgctaa agaaattctt gc                                            22

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 7
cgcggatcct gtgtcaactt atgccgc                                       27

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 8
gtggctgcag tgtggttgga acgc                                          24

DETECTION OF NUCLEIC ACID SEQUENCE VARIATIONS USING PHASE MU TRANSPOSASE This application claims the benefit of the filing date of U.S. Provisional Application Ser. No. 60/457,934, filed Mar. 28, 2003, which is incorporated by reference herein in its entirety.

FIELD OF THE INVENTION

This invention relates generally to the detection of sequence variations in nucleic acids, e.g., the detection of mutations in DNA.

BACKGROUND INFORMATION

Methods for detecting small mutations such as single base substitutions in nucleic acids provide powerful tools for a variety of purposes, including cancer diagnosis and prognosis, perinatal screening for inherited diseases, and the analysis of genetic polymorphisms, for example for genetic mapping or identification purposes. A mutant nucleic acid that includes a single nucleotide change or multiple nucleotide changes will form base pair mismatches after denaturation and subsequent annealing with the corresponding wild type and complementary nucleic acid.

Several types of methods have been used to detect such nucleic acid mismatches, but they often exhibit drawbacks. For example, methods that depend on mismatch selective DNA binding proteins lack easy mapping capabilities. Methods based on conformation-dependent DNA electrophoretic mobility difference induced by small sequence changes, such as SSCP (single-strand conformation polymorphism) and DGGE (denaturing gradient gel electrophoresis) are widely used. They, however, are unable to show the location of mutations; and DNA length limitations and the need for optimization for individual experiments make them cumbersome ( Cotton et al. (1998), *Mutation detection: a practical approach* (IRL Press at Oxford University Press, New York). Other methods that use chemicals or RNAses as cleavage agents at heteroduplex sites either can detect only a subset of mutations, involve hazardous materials or require multiple steps (Myers et al (1985), *Science* 229, 242-7; Cotton et al. (1988), *Proc Natl Acad Sci USA* 85, 4397-401). Another method uses T4 endonuclease VII as heteroduplex-cleaving enzyme (Youil et al. (1995), *Proc Natl Acad Sci USA* 92, 87-91; Mashal et al. (1995), *Nat Genet* 9, 177-83).

Transposons are genetic elements that move from one location in the genome to another. The transposition process involves DNA cleavage at the 3' ends of the transposon followed by the rejoining of the 3'OH termini to a new target DNA site (Mizuuchi, K. (1992), *Annu Rev Biochem* 61, 1011-51). These steps are catalyzed by the element-specific transposase proteins. Phage Mu propagates by replicative transposition that is catalyzed by the MuA transposase. While this reaction is physiologically controlled by a number of regulatory cofactors, the DNA cleavage and joining reactions can be promoted in vitro, by the transposase protein and a DNA fragment with the right end sequence of Mu genome (Savilahti et al. (1995), *Embo J* 14, 4893-903; Mizuuchi et al. (1989), *Cell* 58, 399-408; Craigie et al. (1986), *Cell* 45, 793-800). Mu can transpose to essentially any DNA sequence.

The inventors report herein that, unexpectedly, Mu displays a dramatic preference for insertion into mismatched DNA sites. This newly identified specificity allows for methods to detect and map mismatched DNA sites, hence genetic mutations, in the presence of a large excess of nonspecific DNA.

BRIEF DESCRIPTION OF THE DRAWINGS

FIG. 1A illustrates the structure of a Mu-end DNA fragment (a) and of three typical target DNA fragments (b, c and d). a: The Mu-end DNA fragment contains the first 51 bp of the Mu R-end sequence, including the RI and RII MuA-binding sites (shaded). This substrate DNA is "pre-cleaved" and is capable of undergoing strand transfer without further processing. b: The standard target DNA fragment (76 bp). c: The mismatch target DNA fragment. This is identical to b except for mismatch bases (X and Y). d: The bulge target DNA fragment. This is identical to b except for bulged bases (Z).

FIG. 1B shows the effect of mismatch or bulge in the target DNA on the strand transfer products. The Mu end DNA fragment was labeled at the 5'-end of the strand to be transferred. ST stands for strand transfer product. Two dominant bands in lane 3 correspond to 91 and 92 nt.

FIG. 1C shows the location of the target cleavage site on the mismatch containing DNA. Reactions were carried out with regular (lane 1, 2) or mismatch target DNA (lane 3, 4) labeled at either the 5'-end of top strand (lane 1, 3) or bottom strand (lane 2, 4). The predominant bands in lane 3 and 4 correspond to 35 and 36 nt, respectively.

FIG. 1D shows a schematic of the strand transfer product with mismatch bases centered in the 5 bp targeted sequence. Mu end DNA is shown as dark lines and target DNA as gray lines.

FIG. 2A shows the percentage of the radioactive intensity for the mismatch-targeted products to total radioactive intensity of ST products (60 to 120 nt).

FIG. 2B shows the percentage of the strand transfer products targeted to consecutive mismatches. Consecutive mismatches were made by changing adjacent bases in the bottom strand to the same base as on the top strand.

FIG. 4A is a schematic diagram of mutation detection in the CFTR gene. The human genome harbors two alleles of CFTR gene. The normal CFTR gene has a GGA codon which codes G542 (left panel). The DNA from the patient we used has a homozygous nonsense mutation (M/M, GGA to TGA) at this locus. The DNA from the sibling of the patient has a heterozygous mutation (N/M) at the same position. When the DNA with the heterozygous mutation is used as a template for PCR, the PCR product will have two kinds of mismatch DNA after the amplification reaches a plateau (middle panel). For the detection of the homozygous mutation, PCR using the patient DNA (M/M) mixed with normal DNA (N/N) as a template will produce the mismatch DNA. Those mismatch DNAs will be targeted by Mu to generate 102 nt and 111 nt strand transfer products (right panel). Grey lines are exon 11. Zebra lines are adjacent introns. Black lines are Mu end DNA. Small arrows are primers for PCR. Asterisks are labeled positions.

FIG. 4B shows an autoradiograph of transposition reaction products with the CFTR gene as the target. The template DNA used for PCR are indicated at the top.

DESCRIPTION OF THE INVENTION

Figure 1A:
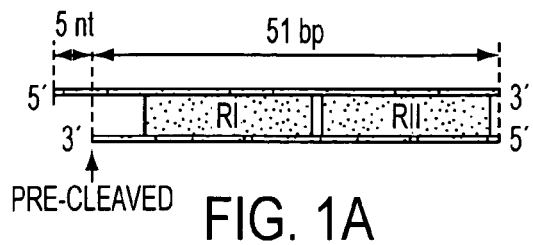
FIGS. 1A-1D show strand transfer with the mismatch target DNA.

The present invention relates, e.g., to a method for detecting a mismatch in a double stranded nucleic acid of interest, comprising (1) contacting the target with (a) a Mu-end nucleic acid and (b) a MuA transposase, under conditions effective for the Mu-end nucleic acid to transpose into the target at about the site of a mismatch, if the target comprises a mismatch, and (2) detecting the location and/or the efficiency of transposition of the Mu-end nucleic acid into the target, wherein transposition of the Mu-end nucleic acid into the target at a predominant site indicates that the target comprises a mismatch (e.g., indicates the presence of a mismatch at about the site of the transposition). The method also allows for precise mapping of the site of the mismatch. The method is preferably performed in vitro (in a cell-free environment), i.e., with isolated reaction components.

The method of the invention (Mu transposition) is a simple, rapid, inexpensive and highly sensitive means of detection of mismatches, even single base substitutions, in cloned or genomic DNA. In a preferred embodiment, in which the mismatch sites are tagged with the Mu DNA sequence, the method offers certain unique advantages. For example, the use of labeled Mu DNA eliminates the need for labeling individual target DNA samples. Further advantages related to this preferred embodiment are discussed below.

This invention relates, e.g., to a method for detecting a mismatch in a double stranded nucleic acid target, comprising a) contacting the target with
i) a Mu-end nucleic acid, and
ii) a phage Mu transposase,
under conditions effective for the Mu-end nucleic acid to transpose into the target at about the site of a mismatch, if the target comprises a mismatch, and
b) detecting transposition of the Mu-end DNA into the target,
wherein transposition of the Mu-end nucleic acid into the target at a predominant site indicates the presence of a mismatch at that site.

In embodiments of this method, the Mu-end nucleic acid is detectable; the Mu-end nucleic acid is detectably labeled; the target nucleic acid is detectably labeled; the target and/or the Mu-end nucleic acid are DNA; the target is generated by polymerase chain reaction (PCR); the mismatch indicates the presence of a mutation; the mismatch indicates the presence of a polymorphism; the method is a method for typing a pathogenic microorganism strain; or the method is a high throughput method.

In another embodiment of the method, the method further comprises c) providing a control duplex nucleic acid comparable to the test double stranded nucleic acid target, but known to be free from mismatches, d) contacting the control duplex with
i) a Mu-end nucleic acid, and
ii) a phage Mu transposase,
under conditions effective for the Mu-end nucleic acid to transpose into the control duplex at about the site of the mismatch, if the control duplex comprises a mismatch,
e) detecting transposition of the Mu-end DNA into the control duplex, and
f) comparing the transposition of the Mu-end nucleic acid into the test target and into the control duplex,
wherein an increased incidence of transposition of the Mu-end nucleic acid into the test target at a predominant site compared to the incidence of transposition of the Mu-end nucleic acid into the control duplex at the corresponding site indicates the presence of a mismatch at that site in the test target. In an embodiment of this method, the detection and comparing comprise (i) separating by size the products of the transposition reactions, and (ii) comparing the amount and sizes of the products from the treated test target with the products from the treated control duplex, as an indication of the presence or absence of a mismatch in the test target.

As noted above, in some embodiments, a control duplex (a double stranded nucleic acid which is free from mismatches, such as a wild type nucleic acid), is processed in parallel with a test double stranded nucleic acid target, and one or more members of each of the two sets of transposition products are compared. However, in other cases, such a control is not used. For example, the products from a transposition reaction with a test target may be compared to a standardized value, or to no control at all. Alternatively, the transposition products from several test nucleic acids may be compared to one another, e.g., as described in Example IIIB ("Unknown mutations").

Another embodiment is method for detecting a mismatch between a first nucleic acid strand and a second nucleic acid strand, comprising forming a duplex between a molecule of said first strand, or a portion thereof, and a molecule of said second strand, or a portion thereof, and contacting said duplex with a Mu-end nucleic acid and a phage Mu transposase, and proceeding as above. In this method, the duplex may be formed by (a) amplifying a portion of the first strand, (b) amplifying a portion of the second strand, and (c) forming a duplex between an amplification product of the first strand and an amplification product of the second strand. In a preferred embodiment, the first strand and the second strand are co-amplified by PCR.

Another aspect of the invention is a method as above, which further comprises determining the location of a mismatch in a double stranded nucleic acid, comprising a) contacting the target with
i) a Mu-end nucleic acid, and
ii) a phage Mu transposase,
under conditions effective for the Mu-end nucleic acid to transpose into the target at about the site of a mismatch, if the target comprises a mismatch,
wherein the transposition comprises nicking one strand of the target at about the site of the mismatch and ligating the 3' terminus of the proximal end of the Mu-end nucleic acid to the 5' terminus of the nicked target strand, thereby generating four transposition products, and
b) determining the length of one or more of the transposition products,
wherein the length of one or more of the transposition products indicates the site of the mismatch.

Another embodiment further comprises determining the location of a mismatch in a double stranded nucleic acid, comprising forming a duplex between a molecule of said first strand, or a portion thereof, and a molecule of said second strand, or a portion thereof, and contacting said duplex with a Mu-end nucleic acid, and a phage Mu transposase and proceeding as above.

Another aspect of the invention is a method for detecting the presence of a mutation or polymorphism in a nucleic acid of interest, comprising a) generating a double stranded nucleic acid target (forming a duplex), in which a first strand comprises a portion of the DNA of interest, which may contain the mutation or polymorphism, and a second strand comprises a comparable portion of a wild type (non-mutant) DNA, b) contacting the double stranded nucleic acid target with
  i) a Mu-end nucleic acid, and
  ii) a phage Mu transposase,
under conditions effective for the Mu-end nucleic acid to transpose into the target at about the site of a mismatch, if the target comprises a mismatch, and c) detecting transposition of the Mu-end DNA into the target, wherein transposition of the Mu-end nucleic acid into the target at a predominant site indicates the presence of a mutation or a polymorphism in the nucleic acid of interest.

In embodiments of this method, the mutation is diagnostic of a disease or a condition, or a susceptibility to the disease or condition; the mutation is a polymorphism; the mutation is in an essential gene; the mutation is in a CFTR, APC, p53, Rb, BRCA1, HMSH1, or HMLH1 gene; the method is a method for screening an embryo for the presence of a mutation, for detecting the presence of a known mutation in a gene of interest, for detecting the presence of a previously unidentified mutation in a gene of interest, or for diagnosing the presence or absence of a tumor-promoting mutation.

Another aspect of the invention is a method of detecting the presence of a mutation or polymorphism in a DNA of interest, comprising a) amplifying a portion of the DNA of interest suspected of containing the mutation or polymorphism by PCR and, optionally, co-amplifying the same portion of a comparable control DNA which lacks any mutation at that site, to form a duplex, b) contacting the duplex with
  i) a Mu-end nucleic acid, and
  ii) a phage Mu transposase,
under conditions effective for the Mu-end nucleic acid to transpose into the target at about the site of a mismatch, if the target comprises a mismatch, c) separating by size the reaction products of the transposition, and d) determining the size of the transposition product(s) ligated to the Mu-end DNA, wherein transposition of the Mu-end nucleic acid into the target at a predominant site indicates the presence of a mutation in the nucleic acid of interest, and wherein the size of the transposition product(s) indicates the site of the mutation, and wherein the presence of a predominant site of Mu-end DNA integration when the DNA of interest is subjected to PCR in the absence of the control DNA indicates that the DNA of interest is heterozygous for the mutation, and wherein the presence of a predominant site of Mu-end DNA integration only when the DNA of interest is co-amplified by PCR in the presence of the control DNA indicates that the DNA of interest is homozygous for the mutation.

In embodiments of this method, the size separation is performed by electrophoresis; the electrophoresis is on an acrylamide gel, an agarose gel, or in a capillary tube. In another embodiment, following step b) above, the product(s) of the transposition reaction are amplified using one Mu end specific primer and one primer specific to a region of interest from the target nucleic acid.

Another aspect of the invention is an in vitro reaction mixture comprising a Mu-end nucleic acid (e.g, a detectable Mu-end nucleic acid), a phage Mu transposase, and a double stranded target DNA comprising a mismatch.

Another aspect of the invention is a kit for determining if a double stranded nucleic acid of interest contains a mismatch, comprising a Mu-end nucleic acid, a phage Mu transposase, and means for determining if the Mu-end nucleic acid transposes into the target at a predominant site and/or instructions for determining if the double stranded nucleic acid contains a mismatch. Other optional components of the kit are oligonucleotide primers suitable for amplification of a nucleic acid fragment comprising a portion suspected of containing a mutation, means for labeling the Mu-end nucleic acid, and/or a preformed gel Another aspect of the invention is a method for detecting a mismatch in a double stranded nucleic acid target, comprising (1) contacting the target with (a) a phage D108-end nucleic acid, and (b) a phage D108 transposase, under conditions effective for the D108-end nucleic acid to transpose into the target at about the site of a mismatch, if the target comprises a mismatch, and b) detecting transposition of the D108-end DNA into the target, wherein transposition of the D108-end nucleic acid into the target at a predominant site indicates the presence of a mismatch at about that site.

The order and numbering of the steps in the methods described herein are not meant to imply that the steps of any method described herein must be performed in the order in which the steps are listed or in the order in which the steps are numbered. The steps of any method disclosed herein can be performed in any order which results in a functional method. Furthermore, the method may be performed with fewer than all of the steps, e.g., with just one step.

In the assays described herein, a given double stranded target may or may not comprise a mismatch. In a general sense, this invention relates to methods to determine if a sample contains a mismatch, irrespective of whether a mismatch is detected.

By way of illustration, the general method of the invention is outlined in FIG. 1. FIG. 1A shows the structures of typical nucleic acid (in this example, DNA) components used in the method. FIG. 1A-a shows the structure of a preferred Mu-end DNA fragment used in the method. During Mu-mediated transposition in vivo, MuA transposase cleaves the two ends of the Mu genome at the junction between the Mu genome and the flanking sequence derived from the host organism of the phage on one strand, generating 3'-OH termini located precisely at the Mu genome termini. A "Mu-end DNA," as used herein, refers to a fragment from the right (R) end of a double stranded Mu that can function in an in vitro Mu-mediated transposition reaction according to this invention. The minimum size of the Mu-end DNA that functions efficiently under the reaction conditions utilized in this invention is approximately 50 base pairs excluding the several nucleotide extension on the 5'-end of the non-transferred strand. While shorter length of the Mu DNA facilitates direct size measurement of the ligated transposition product(s), if desired in certain embodiments of this invention, additional nucleic acid of any sequence or length, and/or other material of choice, can be added to the distal end of the Mu DNA. Preferred Mu-end DNA fragments used in the method of the invention, such as that shown in FIG. 1A-a, have a "pre-cleaved" 3' end and a short 5' overhang. The Mu-end DNA fragment shown in the figure comprises the first 51 bp of the Mu R-end sequences. The upper strand is sometimes referred to herein as the "non-transferred" strand, and the lower strand as the "transferred" strand. The end of the DNA that transposes into the target is sometimes referred to herein as the "proximal" end, and the other end as the "distal" end.

Figure 1B:
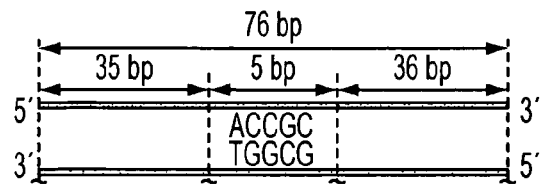
Figure 1B:
Figure 1B:
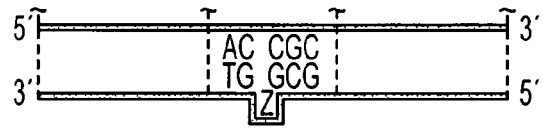
Figure 1B:
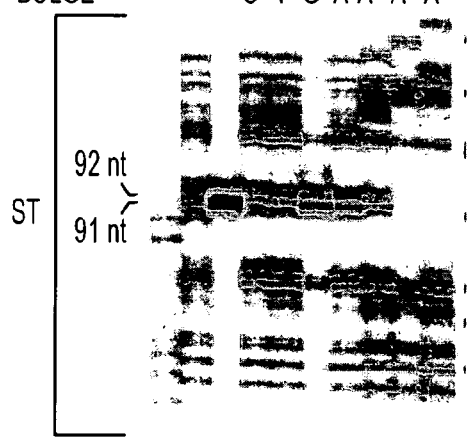
Figure 1B:
Figure 1C:
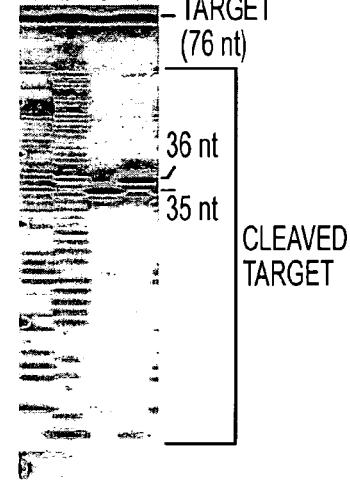

FIGS. 1A-b, c and d illustrate some typical double strand target sequences. FIG. 1A-b shows a homoduplex, in which the 5 nucleotides in the center of the fragment align to form a perfect Watson-Crick base pair match. FIG. 1A-c shows a heteroduplex, in which bases X and Y do not form a Watson-Crick base pair, but form a single bp mismatch. FIG. 1A-d shows a mismatch in which nucleotide(s) Z is unpaired, and forms a "bubble" or loop.

Figure 1D:
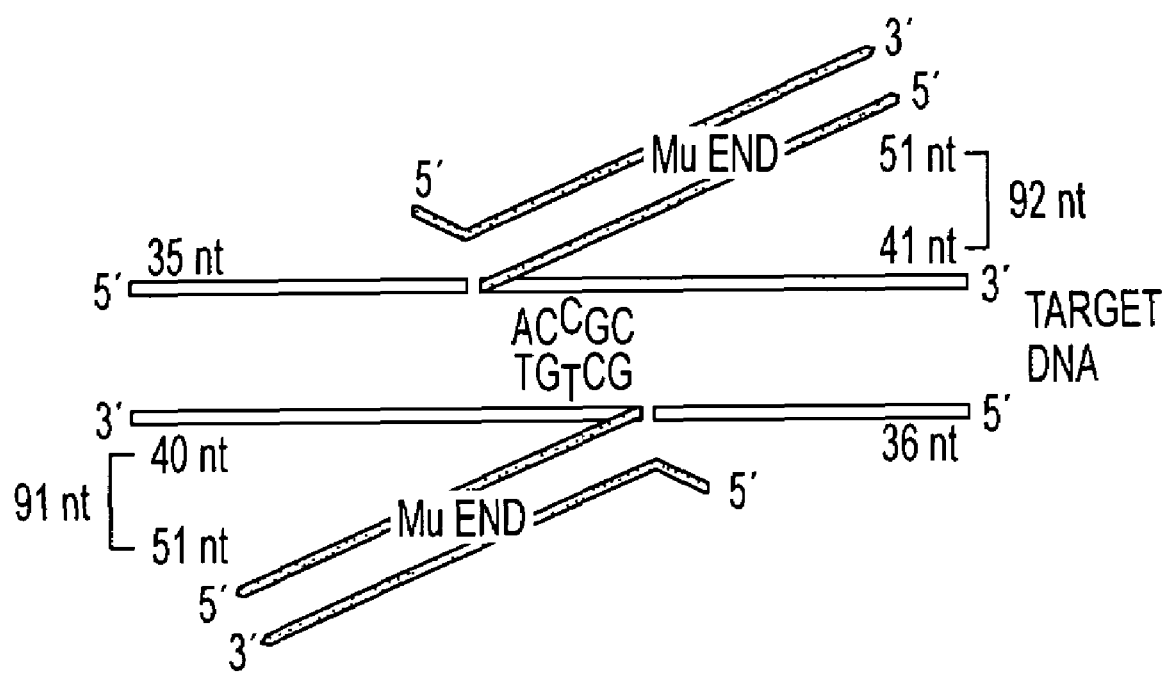

A schematic of the method of the invention is shown in FIG. 1D. The target DNA is the heteroduplex shown in FIG. 1A-c, which has a single base pair mismatch. This target is contacted with the Mu-end DNA and MuA transposase. Looking first at the upper strand of the target, the target is nicked two bases 5' to the site of the mismatch, and the transferred strand of the Mu-end DNA is ligated to the target strand at this position. This ligated DNA strand has a length of 51 nt (Mu-end DNA) plus 41 nt of the upper strand of the target DNA, or a total of 92 nt. The remainder of the upper strand of the target is 35 nt in length. A comparable strand transfer occurs for the lower strand of the target, to yield a ligated DNA of 40 nt plus 51 nt, or 91 nts; the remaining stand is 36 nt in length. Thus, four "transposition products" are formed during each transposition reaction, two from each of the of the strands of the double stranded target.

As is evident from FIG. 1D, the location of the target cleavage and ligation to Mu-end DNA on the two strands of the target takes place with a five nucleotide stagger (5'-extension) and the preferential transposition at the mismatch places the mismatched nucleotide at the center of the five nucleotides. With a single nucleotide mismatch, the nick is therefore two nucleotides 5' from the mismatch on each strand. Therefore, the "ligated product strand" is two nucleotides longer than the sum of the length of the transferred strand of Mu DNA and the distance on the target from the site of mismatch to each end. On the other hand, the cleaved target strand that remains unligated would be two nucleotides shorter. When there are multiple consecutive nucleotide mismatches, the product size distribution would accordingly spread. When referring herein to the transposition of a target "at about the site of a mismatch," it is meant that the transposition occurs within the range of distances noted above, e.g., two nucleotides 5' to the site of the mismatch.

FIG. 1B shows a visualization of the strand transfer schematically represented in FIG. 1D. The 5' end of the lower strand (transferred strand) of the Mu-end DNA is labeled. Following contact of the target with the labeled Mu-end DNA and the transposase, transposition occurs as indicated in the schematic, and the resulting DNA products of the transposition event are separated by electrophoresis on a denaturing acrylamide gel and visualized. When a 76 bp DNA homoduplex (lacking any mismatches) was used as the target, the length of the resulting recombinant fragments was randomly distributed from 68 bp to 115 bp (FIG. 1B, lane 2). This indicates that the Mu DNA was transferred to sites throughout the target DNA, except at the 5'-terminal 12 nt and 3'-terminal 17 nt. When the target DNA contained a single base pair mismatch, insertions to the normal duplex sites were suppressed and nearly 90% of the strand transfer products were either 91 nt- or 92 nt-long (FIG. 1B, lane 3). Thus, the method allows one to determine the presence of a mismatch and its location in the DNA fragment in a single step, in a highly specific manner. This experiment is discussed in more detail in Example I.

Example II shows by several procedures that single mismatches having all 8 of the possible base pair mismatches are efficiently detected by the method, as are mismatches having up to five unmatched base pairs (bubbles); and that mismatches can be detected selectively in the presence of a large excess of target heterogeneous sequence.

Known mutations can be readily detected by the inventive method. Example IIIA examines the DNA of (1) a patient suffering from cystic fibrosis (CF), who has a homozygous mutation in the cystic fibrosis transmembrane conductance regulator (CFTR) gene; (2) her non-symptomatic sister, who has a heterozygous version of the mutation; and (3) a wild type control. DNA targets were generated by PCR amplification from genomic DNA in a region where the mutation was expected to be present. The method of the invention clearly detects (and confirms the mapping of) the mutation.

Furthermore, the method allows one to distinguish between a homozygous and a heterozygous mutation. When DNA of the heterozygous sister was amplified by PCR, a heteroduplex mismatch DNA fragment was generated during the PCR. DNA from the homozygous subjects (the normal control and the homozygously mutated patient) did not give rise to heteroduplex fragments during PCR. However, when the patient's DNA was co-amplified with the wild type control DNA, a heteroduplex (mismatch) DNA fragment was generated. Thus, homozygous mutations can be distinguished from heterozygous mutations by the requirement for co-amplification of the non-mutant sequence.

The method of the invention can also be used to detect unknown mutations. Example IIIB shows that the detection of mutations within the highly polymorphic HLA region can be accomplished with the inventive method. Moreover, it shows that the method can reliably detect multiple mismatches simultaneously.

In some embodiments, a control duplex (double stranded nucleic acid, which is free from mismatches), such as a wild type nucleic acid, is processed in parallel with a test target double stranded nucleic acid, and the two sets of transposition products are compared. However, in other cases, such a control is not used. For example, the transposition products from a transposition reaction with a test target may be compared to a standardized value. Alternatively, the transposition products from several test nucleic acids may be compared to one another, e.g., as described in Example IIIB ("Unknown mutations").

In one embodiment of the invention, the precise location of the mismatch is determined. As noted above, four "transposition products" are generated during each transposition reaction. Determination of the length of any of these four transposition products can be used to determine the location of the mismatch. In other words, the information is redundant and which particular transposition product is detected depends on which strand end of which reaction partner, Mu DNA or the target, is labeled for the purpose of detection. For example, if the transferred strand of Mu is labeled, the length of the product to be detected would be the length of the ligated nucleic acid, or more specifically, the length from the 3'-end of the target to the mismatch plus two nucleotides (as discussed above) plus the length of the transferred strand of the pre-cleaved Mu-end DNA. Because the target has two strands, there will be two products detected in this manner, each reflecting the distance from the mismatch to one of the two target DNA ends plus the Mu DNA length. However, without further analysis, there remains a two-fold ambiguity concerning which of the two target ends is closer to the position of the mismatch. In principle, the same products can be detected if instead of the Mu DNA, the 3'-ends of the target are labeled. However, in this case, one has an option of labeling only one 3'-end of the target of interest, avoiding the ambiguity of the two possible positions of the mismatch that is detected. Alternatively, if the 5'-end of the target is labeled, the product of interest that is detected would be the cut off target strands from the 5'-end to the site of the mismatch minus two nucleotides (as discussed above). This fragment (one of the four transposition products) is not ligated to the Mu DNA, but nevertheless, its length reflects the location of the transposition reaction on the target, and thus of diagnostic value for the presence of a mismatch and its location. In essence, for each strand there are two lengths of the transposition products of interest, namely, the half of the target strand that is ligated to the transferred strand of Mu, and the other half of the target strand that does not get ligated to Mu DNA. Therefore, depending on the labeling conditions, the length of any of the four transposition products can be determined in order to identify the location of the mismatch. Methods for labeling the strands of the Mu-end DNA or the 5' or 3' ends of the target are discussed elsewhere herein.

The term "mismatch," as used herein, means that a nucleotide in one strand of a nucleic acid does not or cannot pair through Watson-Crick base pairing and π stacking interactions with a nucleotide in an opposing complementary nucleic acid strand. (As used herein, the singular forms "a," "an," and "the" include plural referents unless the context clearly dictates otherwise. For example, "a" mismatch may contain one or more unpaired nucleotides.) For example, one or more of the following may be present: (1) DNA nucleotide pairing other than A-T or G-C occurs, e.g., nucleotide paring such as A-C, A-G, A-A, T-C, T-G, T-T, G-G, or C-C occurs; (2) multiple consecutive mismatches, sometimes referred to as bubbles, of at least 5 nucleotides.

A mismatch may reflect the presence of a mutation, which can arise, for example, from a DNA replication error, mutagenesis, deamination of 5-methylcytosine, DNA recombination, or the like. A "mutation," as used herein, refers to a nucleotide sequence change (i.e., a single (point mutation) or multiple nucleotide substitution, deletion, insertion or inversion) in a nucleic acid sequence. A nucleic acid which bears a mutation has a nucleic acid sequence that is different in sequence from that of the corresponding wild-type population.

A target to be analyzed may be derived from any source suspected of harboring at least one mutation, including genomic or cloned DNA. The nucleic acid may be derived from any eukaryotic, eubacterial, or archaeal cell, or a virus. Preferably, the nucleic acid is derived from a vertebrate, more preferably a mammal, including, e.g., farm animals, domestic animals, research animals, or the like. Most preferably, the nucleic acid is derived from a human.

A double stranded (duplex) target nucleic acid may be in any form that can serve as a substrate for the MuA transposase in the inventive method. In a preferred embodiment, both strands of the duplex are DNA. However, one or both strands may also be, at least in part, RNA, PNA (peptide nucleic acid), LNA (linked nucleic acid) or a modification thereof. For example, the nucleic acid may comprise one or more nucleotides that are joined via various known linkages, e.g., ester, sulfamate, sulfamide, phosphorothioate, phosphoramidate, methylphosphonate, carbamate, etc. See, e.g., U.S. Pat. No. 5,378,825. Any desired nucleotide or nucleotide analog can be incorporated, e.g., 6-mercaptoguanine, 8-oxo-guanine, etc. Various other modifications can be made to the nucleic acids, such as attaching detectable markers (avidin, biotin, radioactive elements, fluorescent tags and dyes, energy transfer labels, energy-emitting labels, binding partners, etc.) or moieties which improve hybridization, detection, and/or stability. The discussion herein is generally directed toward "DNA" duplexes. However, one of skill in the art will recognize that the discussion also applies to other suitable forms of nucleic acid duplexes.

As noted above, one embodiment of the invention is a method of detecting a mismatch between a first nucleic acid and a second nucleic acid strand, comprising (a) forming a duplex between a molecule of the first strand, or a portion thereof, and a molecule of the second strand, or a portion thereof; (b) contacting the duplex with (i) a Mu-end nucleic acid and (ii) a MuA transposase, under conditions effective for the Mu-end nucleic acid to transpose into the target, at about the site of a mismatch, if the target contains a mismatch; and (c) detecting transposition of the Mu-end nucleic acid into the target, wherein transposition of the Mu-end nucleic acid into the target at a predominant site indicates that the target comprises a mismatch (e.g., indicates the presence of a mismatch at about the site of the transposition event).

In the case of a subject or sample that is heterozygous for a site, e.g., a mutation of interest, the first and second strands can be derived from the subject or sample. Where a subject or sample is homozygous for a site of interest it will often be desirable to supply strands for duplex formation from another source (a comparable source). In preferred embodiments, the first strand is derived from a subject having or being at risk for a mutation, or susceptible to a particular condition related to the mutation; and the second strand has a wild-type sequence for the mutation. In embodiments of this aspect, the first strand encodes the sense or anti-sense strand of a mutant allele derived from a subject having or being at risk for the mutation, or susceptible to a particular condition related to the mutation; the second strand encodes the sense or antisense strand of a wild type allele for the mutation; the second strand is not derived from the subject at risk for a mutation; and/or the second strand is derived from a subject not at risk for a mutation or for a disorder associated with a mutation. The second strands are comparable to the first strands, except that they lack the mutation.

A target DNA duplex may be prepared by any of a variety of conventional procedures. Generally, one selects a region (portion; fragment) of interest in a sample (test sample) that is suspected of harboring a potential mutation, isolates it, and optionally amplifies it. One strand of the isolated DNA fragment from the test sample is annealed to a complementary strand of a control (reference; wild type) sample. If the test sample comprises a mutation, the resulting double stranded DNA will form a heteroduplex; if the test sample does not comprise a mutation the resulting double stranded DNA will form a homoduplex.

By an "isolated" nucleic acid is meant herein a nucleic acid segment or fragment which is not immediately contiguous with (i.e., covalently linked to) both of the nucleic acids with which it is immediately contiguous in the naturally occurring genome of the organism from which the nucleic acid is derived. The term, therefore, includes, for example, a nucleic acid which is incorporated into a vector, for example, a bacteriophage, virus, or plasmid vector capable of autonomous replication. The term "isolated nucleic acid" may also include a nucleic acid which is substantially purified from other nucleic acids, such as a nucleic acid fragment produced by chemical means, selective amplification, or restriction endonuclease treatment. Because the detection assays of the invention may be used to simultaneously analyze more than one DNA sequence, isolation and purification are not necessarily required, but may be carried out if desired.

By "heteroduplex" is meant a structure formed between two annealed, complementary nucleic acid strands (e.g., the annealed strands of test and reference nucleic acids) in which one or more nucleotides in the first strand are unable to appropriately base pair with those in the second opposing, complementary strand because of one or more mismatches. The term "complementary," as used herein, means that two nucleic acids, e.g., DNA or RNA, or two strands of DNA, contain a series of consecutive nucleotides which are capable of forming matched Watson-Crick base pairs to produce a region of double-strandedness. Thus, e.g., adenine in one strand of DNA pairs with thymine in an opposing complementary DNA strand or with uracil in an opposing complementary RNA strand. Or guanine in one strand of DNA or RNA pairs with cytosine in an opposing complementary strand. The region of pairing is referred to as a duplex. A duplex may be either a homoduplex or a heteroduplex.

Many conventional procedures are available for preparing a suitable target duplex to be analyzed.

In a preferred method, particularly when a suspected mutation is in genomic DNA, a DNA template suspected of harboring at least one DNA mutation and for which at least a partial DNA sequence is known is used as a source of PCR amplified test DNA. A DNA template for this purpose includes a region suspected of harboring at least one DNA mutation and also includes sufficient DNA flanking the suspected mismatch to serve as a template for DNA oligonucleotide primer hybridization and PCR amplification. PCR amplification is performed by first hybridizing two oligonucleotide primers to the template harboring the mutation, then completing multiple rounds of PCR amplification. The design of the two oligonucleotide primers is guided by the DNA sequence flanking the suspected mutation site and at least two important parameters: DNA oligonucleotide primer size and the size of the intervening region between the 3' ends of the DNA oligonucleotide primers hybridized to the template. Preferably, an oligonucleotide primer will be at least about 12 nucleotides in length, more preferably, between about 15 and 50 nucleotides in length inclusive, and most preferably, between about 15 and 25 nucleotides in length inclusive.

The size of the intervening region between the 3' ends of the two oligonucleotides hybridized to the template will be governed by, i. a., the well known size limitations of templates amplified by PCR and (when a gel is used to resolve transposition products) the resolving power of the particular gel used to detect the transposition products. The intervening region between the 3' ends of the two oligonucleotides hybridized to a template will vary according to the needs of the assay. The minimum total length of the target DNA that can function is about 30 base pairs and there is no theoretical upper limit. Thus, the minimum length between the primers can be only a few base pairs if one wishes to focus on a specific mutation at a known location. For a survey of a large area, the only practical limit is imposed by the efficiency of the PCR reaction. Both the poor amplification efficiency of very long molecules and the limited accuracy of the amplification can put an upper practical size limit, because mistakes during amplification generate random mismatches. Generally, a test fragment size is selected such that the sizes of the products of the transposition reaction can be readily separated, e.g., by gel electrophoresis. Those skilled in the art will appreciate that where the flanking DNA sequence is only partially known, a degenerate DNA oligonucleotide primer may be used to prepare test DNA by PCR amplification.

Example III illustrates procedures to PCR amplify a suitable portion of DNA from the genomic DNA of a patient suffering from cystic fibrosis (having a homozygous mutation in the CFTR gene) and from a sibling carrying a heterozygous mutation at that site, and to prepare suitable target duplexes for analysis by methods of the invention.

Suitable primers and conditions for PCR amplification can be readily determined by a skilled worker. See, e.g., the discussion in limes et al., eds. *PCR Protocols: A Guide to Methods and Applications*, 1990, Academic Press, San Diego, Calif. DNA amplification conditions can be optimized empirically by standard techniques for each primer set with respect to magnesium concentration, annealing temperature, primer/template combination, etc.

As shown in Example III, if one PCR amplifies a fragment from a subject having a heterozygous mutation, a heteroduplex fragment is generated during the course of the PCR amplification. After a suitable number of rounds of amplification, approximately 50% of the resulting double stranded fragments are heteroduplexes. If desired, an additional final step of denaturing and reannealing may be performed to ensure the maximum yield of heteroduplex.

DNA amplified from a subject that is homozygous for a given mutation will, of course, not give rise to a heteroduplex. Thus, it is generally desirable to co-amplify a fragment from a test subject with DNA from a control subject that is known not to contain a mutation in the region being amplified. In this manner, if the subject has a homozygous mutation, a heterodimer will be formed during the PCR co-amplification, in which one strand has the mutation from the subject, and the other strand lacks the mutation. Suitable conditions for such co-amplification are conventional.

In other embodiments, DNA fragments that comprise the two strands of a target heteroduplex are amplified individually (separately), purified, and denatured and reannealed together, to form a duplex fragment. For example, the two DNAs may be combined in a standard DNA annealing buffer, mixed at an appropriate ratio (for example, in equimolar amounts), subjected to heat denaturing conditions, and slowly cooled to allow renaturation, following conventional procedures.

One method to isolate and amplify a DNA suspected of harboring at least one DNA mutation is to subclone the DNA into a suitable cloning vector and amplify it using known DNA oligonucleotide primers which hybridize to the cloning vector and are adjacent to the insertion site of the DNA template. In this instance, no template DNA sequence information is required because the DNA oligonucleotide primers used for PCR amplification hybridize to a vector of known DNA sequence and not the inserted template DNA. For example, the Bluescript.TM. vector can be used to sub-clone a DNA template into an acceptor site according to the manufacturer's instructions (Stratagene Cloning Systems, La Jolla, Calif., Product Catalogue, (1992)). The T7 and T3 DNA primers of the Bluescript vector can be used to PCR amplify the inserted DNA template (or concomitantly to sequence the inserted DNA template). Other commercially available sub-cloning vectors may also be used. These include, without limitation, phage lambda based insertion vectors and other prokaryotic and eukaryotic vectors (e.g., bacteriophage, insect virus, or animal virus based vectors described by Stratagene, supra.)

Methods for cloning DNAs, or for any of the molecular biological methods used in conjunction with the invention, are conventional, and are described, e.g., in Sambrook, et al. (1989), *Molecular Cloning, a Laboratory Manual*, Cold Harbor Laboratory Press, Cold Spring Harbor, N.Y.; Ausubel et al. (1995). *Current Protocols in Molecular Biology*, N.Y., John Wiley & Sons; Davis et al. (1986), *Basic Methods in Molecular Biology*, Elseveir Sciences Publishing, Inc., New York; Hames et al. (1985), *Nucleic Acid Hybridization*, IL Press; Dracopoli et al. *Current Protocols in Human Genetics*, John Wiley & Sons, Inc.; and Coligan et al. *Current Protocols in Protein Science*, John Wiley & Sons, Inc.

In an alternative method, a vector which includes a DNA insert bearing at least one DNA mutation may be first amplified by propagation in bacteria, phage, insect, or animal cells prior to PCR amplification (see Sambrook et al., supra). If sufficient DNA is available (i.e., at least 1 nanogram), the PCR amplification step can be eliminated.

In yet another example, RNA suspected of bearing at least one mutation may be purified from cells or tissues by techniques well-known in the art. For example, RNA may be optionally purified by olido-dT chromatography to prepare mRNA (see, for example, Sambrook et al., supra and Ausubel et al., supra). In cases where ribosomal RNA is the subject of analysis or a particular mRNA is in abundance, oligo-dT chromatography will not be necessary. Purified RNA or mRNA is heat denatured in order to ensure complete single-strandedness and hybridized with control DNA (i.e., a reference cDNA) in order to form RNA:DNA heteroduplexes. Methods for forming RNA:DNA duplexes are well known in the art and have been described in detail (see, e.g., Sambrook et al., supra). After formation of an RNA:DNA heteroduplex, the method of the invention may be used to detect mismatches produced by mispairing between the cDNA and the RNA. Alternatively, the mRNA may be converted to cDNA, using conventional reverse transcription procedures, amplified by any of the methods described herein, and subjected to analysis by a method of the invention.

If desired, the double stranded target DNA may be labeled with a detectable moiety. For example, one can independently PCR amplify a control (or wild type) DNA and a test (or mutant) DNA with labeled primers, and denature and renature the amplified products in such a way that only certain desired ends of the DNA are labeled. For example, for the first nucleic acid sample (for example, the control or wild-type DNA), one of the following pairs of PCR primers is used: for radioactivity-based assays, one 5'-biotinylated primer and one unmodified primer, or two biotinylated primers; or, for fluorescence-based assays, one 5'-biotinylated primer and one unmodified primer, or two biotinylated primers. For the second nucleic acid sample (for example, the test or mutant DNA), a corresponding set of primers is chosen and labeled as follows: for radioactivity-based assays, primers with 5' OH's are utilized to permit subsequent 5'-radiolabeling, or, for fluorescence-based assays, a 5'-fluoresceinated primer is utilized for amplification of the strand complementary to the wild-type biotinylated strand in combination with one unmodified primer. DNA amplification conditions are optimized by standard techniques for each primer set with respect to concentrations of $Mg^{++}$, DNA template, and primers; conditions for use with unmodified primers sometimes differ from those for use with biotinylated or fluoresceinated primers.

Alternatively, one can label one or both strands of the duplex, e.g., by end-labeling (e.g., 5'-end labeling using bacteriophage T4 polynucleotide kinase and $\gamma$-$^{32}$P-ATP), or by uniform labeling using any radioactive dNTPs of choice. Standard protocols for these techniques are widely available.

If different fluorophores are utilized in the techniques of the invention, multiple mutations may be detected simultaneously, for example, by PCR amplifying different regions of a DNA sample (for example, different exons of interest) using PCR primers that are each labeled with a unique fluorophore that is detectable in the presence of the other fluorescent tags (for example, using an ABI automated sequencing system).

For typical methods to prepare labeled target duplexes, see, e.g., U.S. Pat. Nos. 5,824,471 and 5,958,692.

In a most preferred embodiment, the target duplex is not labeled. Rather, as is discussed elsewhere herein, the Mu-end DNA is detected in the assay, either directly or indirectly.

The test nucleic acid and/or the reference (control) nucleic acid may be derived from any eukaryotic cell, eubacterial cell, bacteriophage, DNA virus, or RNA virus. If desired, a test sample may be prepared from an RNA virus by reverse transcription of the RNA into DNA. Preferred RNA viruses include, without limitation, human T-cell leukemia virus and human immunodeficiency virus (for example, HTLV-I, HTLV-II, HIV-1, and HIV-2). Preferred DNA viruses include, without limitation, any one of the family Adenoviridae, Papovaviridae, or Herpetoviridae. Preferred eubacterial cells include, without limitation, any member of the order Spirochaetales, Kinetoplastida, or Actinomycetales, of the family Treponemataceae, Trypoanosomatidae, or Mycobacteriaceae, and of the species Mycobacterium tuberculosis, Treponema pallidum, Treponema pertenue, Borrelia burgdorferi, or Trypanosoma cruzi.

The test and/or reference nucleic acids may also include an oncogene or a tumor suppressor gene of a eukaryotic (for example, mammalian, preferably human) cell; preferable mammalian oncogenes include, without limitation, abl, akt, crk, erb-A, erb-B, ets, fes/fps, fgr, fms, fos, jun, kit, mil/raf, mos, myb, myc, H-ras, K-ras, rel, ros, sea, sis, ski, src, and yes; preferable tumor suppressor genes include p53, retinoblastoma (preferably RB1), adenomatous polyposis coli, NF-1, NF-2, MLH-1, MTS-1, MSH-2, BRCA-1, BRCA-2, ATM, and human non-polyposis genes.

Alternatively, the test and/or reference nucleic acid may be isolated from any one of the $\beta$-globin, $\alpha$-antitrypsin, 21-hydroxylase, pyruvate dehydrogenase E1 $\alpha$ subunit, dihydropteridine reductase, rhodopsin, $\beta$-amyloid, nerve growth factor, superoxide dismutase, Huntington's disease, cystic fibrosis, adenosine deaminase, $\beta$-thalassemia, omithine transcarbamylase, collagen, bcl-2, $\beta$-hexosaminidase, topoisomerase II, hypoxanthine phosphoribosyltransferase, phenylalanine 4-monooxygenase, Factor VIII, Factor IX, nucleoside phosphorylase, glucose-6-phosphate dehydrogenase, phosphoribosyltransferase, Duchenne muscular dystrophy, von Hippel Lindeau, or the mouse mottled Menkes genes. The nucleic acids may also be derived from any cell cycle control gene, preferably p21, p27, or p16.

The test and/or reference nucleic acid may be any nucleic acid molecule including, without limitation, a restriction enzyme fragment, a sequence produced by amplification via PCR, NASBA, SDA, or any other preparative amplification method, or a sequence propagated in any eukaryotic cell, bacteriophage, eubacterial cell, insect virus (e.g., using a baculovirus derived vector), or animal virus (e.g., using an SV-40 or adenovirus derived vector).

The nucleic acid may be man-made or derived from a naturally occurring source. It may be derived from any suitable source, including, without limitation, a cell (including a cell in culture), tissue, organ, tumor or bodily fluid.

Mu-end DNA can be prepared by any of a variety of conventional procedures. In a preferred embodiment, it is made by annealing two synthetic oligonucleotides, as described in Example 1A. The nucleic acid can take any of the forms discussed above with respect to target duplexes. Preferably, both strands of the Mu-end DNA fragments are DNA.

The Mu-end DNA preferably comprises a "pre-cleaved" 5' single strand overhang as shown in FIG. 1A-a. However, a longer DNA fragment may be present initially in a reaction mixture, and the overhang may be generated during the reaction by cleavage by the transposase. In a preferred embodiment, the Mu-end DNA is a short molecule that is capable of carrying out the in vitro transposition reaction. The 51/56-mer shown in FIG. 1A-a is close to the minimum size; one of skill in the art can readily determine if a shorter (or longer) fragment is active in the transposition reaction. For example, the 5'-extension on the non-transferred strand is not essential, and the other end can be shortened two or three base pairs. The molecule may be shortened even further, but this may cause a reduction of the reaction efficiency. A number of internal sequence changes within the Mu end sequence are tolerated, with different degrees of impact on the reaction efficiency. The RI and RII MuA binding sites indicated in FIG. 1A-a must be present for the efficient in vitro transposition reaction. Longer Mu-end DNA fragments may also be used. There is no upper limit as to the size of such a fragment, except that smaller Mu-end fragments generally give rise to transposition products that are more easily resolved by size than do larger fragments.

If desired, the "transferred" strand of the Mu-end DNA fragment can be labeled with a detectable label. Suitable labels are conventional and include, e.g., any radioactive, fluorescent, chemiluminescent, or chromogenic label which may be directly or indirectly visualized. Also included as useful labels are haptens, such as digoxigenin, that are recognized by antibodies that are themselves detectably labeled. In addition, heteroduplexes may be formed prior to radioactive labeling, and the labeling step carried out either just prior to transposition or after the transposition (taking advantage of the freshly exposed ends for labeling). Example I illustrates a method to end-label the Mu-end DNA strands with $^{32}$P.

The Mu phage transposase can take any of a variety of forms. For example, a full-length transposase may be used. This enzyme may be obtained from commercial sources. For example, Mu transposase is present (in combination with certain specialized Mu transposon constructs) in the kits named "Gene Jumper Kit" and "Gene Jumper oriV Transposon Kit" sold by Invitrogen Life Technologies (1600 Faraday Ave. Carlsbad, Calif. 92008). Alternatively, the enzyme may be prepared according to conventional procedures, such as the published procedure involving standard protein purification column chromatography steps (Baker et al. (1993), *Cell* 74, 723-33).

Alternatively, the transposase may be a functional fragment of the full-length enzyme. Portions of the protein that can be deleted without substantially affecting its ability to perform the in vitro transposition events, include, e.g., an enhancer-binding domain at the N-terminus, and a domain at the C-terminus which interacts with other accessory proteins. The full size Mu transposase is a 663 amino acid protein. The minimum catalytic activity necessary for the purpose of this invention is retained by the truncated protein that starts at the amino acid sequence position 77 and ends at position 604. This protein is commonly referred to as MuA77-604. Other suitable transposase molecules that can be used in methods of the invention include, e.g., MuA77-663 (missing the first 76 amino acids of the full length protein) and MuA77-615 (missing the N-terminal 76 amino acids and the C-terminal 48 amino acids).

The transposase may also comprise variations compared to the wild type protein. Any active variant that retains a substantial ability to perform an in vitro transposition event is acceptable. Suitable variants may comprise, for example, one or more naturally occurring (e.g., through natural mutation) or non-naturally-occurring (e.g., by deliberate modification, such as by site-directed mutagenesis), and either conservative or non-conservative, modifications (e.g., insertions, deletions, additions and/or substitutions). By "conservative substitutions" is meant by combinations such as Gly, Ala; Val, Ile, Leu; Asp, Glu; Asn, Gln; Ser, Thr; Lys, Arg; and Phe, Tyr. Variants can include, e.g., homologs, muteins and mimetics. Many types of protein modifications, including post-translational modifications, are included. Post-translational modifications include naturally occurring or synthetically produced, covalent or aggregative conjugates with other chemical moieties, e.g., glycosyl groups, lipids, phosphates, acetyl groups, etc., as well as cleavage, such as of terminal amino acid(s). See, e.g., modifications disclosed in U.S. Pat. No. 5,935,835. Other active variants may comprise any of a variety of properly folded peptide sequences (e.g., protein domains), added to either the N- or C-terminus of a Mu transposase, including the minimum active Mu transposase. The added sequences can be either naturally occurring or heterologous, and include, e.g., leader, signal, secretory, targeting, enzymatic etc. sequences. Additional examples of such fusion proteins involve epitope-tags and GFP (and its variants)-tags.

A skilled worker can readily test any fragment or variant form of transposase to determine if it is active in a method of the invention.

Many other transposases, including transposases from other Mu-like phages, may also be used in methods of the invention. In particular, phage D 108 is very closely related to Mu, and its end sequence and transposase are both very similar to those of Mu; thus, it is expected that the D108 transposase could be used in the methods of the invention. One of skill in the art can readily determine if a given transposase can be used in a method of the invention.

Conditions effective for in vitro transposase-mediated Mu-end DNA transposition can be optimized empirically. As used herein, the term "transposition" refers to the Mu DNA strand transfer reaction that comprises nicking of a target strand at about the site of a mismatch, and the ligation of the 3' terminus of the "transferred strand" of the Mu-end DNA fragment to the nicked target. The term "at about" the site of a mismatch, as used herein, refers to a transposition event in which the target strand is nicked two nucleotides 5' to the site of a mismatch.

Some of the reaction condition factors that can be varied are discussed in Savilahti et al (1995), *EMBO Journal* 14, 4893-4903. In a most preferred embodiment, the reaction is performed in conditions substantially like those described in Example 1B. The reaction conditions can be varied widely. One of skill in the art can readily determine suitable conditions empirically, without undue experimentation. In a preferred embodiment, the Mu-end DNA fragment is limited with respect to the target DNA. In general, the specificity for the mismatch site of the reaction is improved with slightly higher salts concentrations and lower DMSO concentrations than those discussed in Savilahti et al, supra.

A variety of conventional methods can be employed to detect the transposition of a Mu-end DNA fragment into a target.

In a preferred embodiment, the products of the transposition event are separated by size and then visualized. For example, the single strand DNAs may be separated by electrophoresis, such as on a conventional denaturing gel. Examples include polyacrylamide or agarose gels, depending on the sizes of the fragments to be separated, which are formed in the presence of denaturing agents such as 4-8 M urea or formamide. The gel may be cast as, e.g., a slab gel, or in a capillary tube. DNA fragments containing detectable labels, such as those described elsewhere herein, can be visualized by conventional procedures. Either the target or the Mu-end DNA can be labeled with a detectable label, as is discussed elsewhere herein, to facilitate the visualization. In a preferred embodiment, the 5' end of the "transferred" Mu-end DNA is labeled. The sizes of the products of a transposition reaction are generally determined by comparison to standard size markers. Typical assays using this type of analysis are illustrated in Examples II and III.

Any of the methods of the invention can be adapted to automated, high throughput formats. For example, following a reaction with a 5'-end labeled Mu-end DNA, the products of a transposition reaction can be hybridized to organized arrangements of probes specific for sequential portions along the length of the target DNA, e.g., in wells of microtiter plates or on gene chips. By detecting which probes hybridize to the labeled, ligated DNA, one can readily determine to which portions of the target the Mu-end DNA has ligated, and thus can identify the site of the mismatch.

In a preferred embodiment, the mismatch sites are targeted with an unlabeled Mu-end DNA fragment. The Mu end sequence can then be used as a primer site for PCR amplification of the transposon-tagged DNA. One can make use of this feature in a variety of ways, for example, in devising strategies for analysis of a large target region or a large number of separate regions from a single transposition reaction. After a few rounds of amplification of an expansive target region (followed preferably by a final denaturation/ reannealing step to maximize the fraction of the DNA in the form of heteroduplex DNA) (or even without initial amplification), the transposition step can be carried out and the products used for a second round of amplification using one Mu end primer and a primer specific to each sub-region of interest. This also eliminates the need for using labeled Mu DNA and the ambiguity of the possible mismatch location caused by the detection of both halves of the cleaved products. Another utility of the Mu-end primer would be the convenient sequencing of the reaction products. Not only is the location of the mutation deduced from the fragment size, but the nature of the mutations can be immediately identified by sequencing with a Mu-end primer (Adachi et al. (1987), Nuc. Acids Res.15, 771-84). These features will be especially useful for bulk detection and identification of single nucleotide polymorphism. Finally, bulk isolation of DNA containing mutations would be possible, for example by using biotin-labeled Mu end DNA. High throughput methods using automated sequencers can also be used.

In the case of a small target, comprising a specific mismatch of interest, one can take advantage of the greater efficiency of transposition into the site of a mismatch compared to the background of random transpositions into non-mismatched portions of a target lacking a mismatch. In such a case, one may analyze a transposition reaction without having to separate the reaction products by size. For example, one can subject a reaction mixture in which the Mu-end DNA is labeled at its 5' end and the target DNA affinity-tagged, for example by biotin, and separate the products by affinity to avidin to determine if a given target duplex comprises a mismatch.

In some embodiments, a control reaction is performed, in which a control duplex target comparable to the test duplex target is subjected to the same procedure as is the test duplex. By "comparable target" is meant a double stranded nucleic acid that comprises a strand that is identical to one of the paired structures, but that contains no mismatches. That is, the method further comprises comparing the transposition of the Mu-end nucleic acid into a predominant site of the target to the transposition into that site when the method is performed with a comparable target which lacks a mismatch (or comparing the degree of transposition into the predominant site, or comparing the amount and size(s) of the transposition products, or comparing the number of transposition sites).

Methods of the invention can be used, e.g., in a variety of medical procedures or research, veterinary procedures or research, agricultural applications, forensics (e.g., in human or other animal subjects, or for pathogenic agents) paternity testing, or the like. The methods can also be used to further elucidate the mechanism of transposition. Mismatches can be detected in coding sequences, which can result, e.g., in frame shift mutations, stop codons, or non-conservative amino acid substitutions in a gene, each of which can independently render the encoded protein inactive or otherwise functionally altered. (In some cases, hyper-activity or uncontrolled activity, etc, can cause a problem) (A gene mutation can also be harmless, resulting in a protein product with no detectable change in function. Such mutations are sometimes referred to as harmless gene "polymorphisms"). Alternatively, mutations can be detected in extragenic sequences, which may or may not affect gene function or expression.

Methods of the invention are useful for detecting DNA mutations associated with mammalian diseases (such as various inherited diseases). The mutation may be in any of a variety of genes, or in genetic segments that control their expression, e.g., a gene which affects cell proliferation, such as an oncogene, a gene responsible for a congenital disorder, a gene responsible for cell cycle regulation, a tumor suppressor gene, or the like. For example, one or more mutations in repetitive DNA is associated with the human fragile-X syndrome, spinal and bulbar muscular dystrophy, and myotonic dystrophy. Repetitive DNA from each of these genes can serve as test nucleic acids in the methods described herein. Alternatively, the methods of the invention may be used to detect mutations corresponding to diseases (for example, Marfan's syndrome) for which a standard test is not available or is inconclusive. Among the genes that can be tested are genes which pre-dispose individuals to known diseases, including but not limited to the CFTR, APC, p53, Rb, BRCA1, HMSH1, and HMLH1 genes. Many others will be evident to the skilled worker.

The presence or stage of some disorders (e.g., some disorders characterized by unwanted cell proliferation) are correlated with the presence, in diseased tissue, of characteristic DNA lesions. For example, tissue from many cancers is often characterized by the presence of lesions in oncogenes or tumor suppressor genes. Methods of the invention can be used to evaluate the presence or stage of such a disorder in a subject, e.g., an experimental animal or a human. Methods of the invention can also be used to evaluate the efficacy of a treatment of such a disorder, where the efficacy of the treatment is correlated with the prevalence of a lesion in a tissue of the subject.

The invention can be used to evaluate the past exposure of a subject, e.g., an experimental animal or a human, to agents which result in damage to the subject's DNA. For example, methods of the invention, can be used to evaluate the exposure of a subject to an environmental, occupational, or therapeutic agent which results in DNA lesions. Exposure is correlated with the existence of one or more lesions (which lesions can result in a mismatch) in the subject as measured, e.g., in a tissue sample from the subject.

In another embodiment, the method is used to identify mutations associated with disease conditions that have not been heretofore identified, and can be used to survey even large genes for the presence of mutations, including single base mutations. Similarly, the method can be used to detect neutral polymorphisms in genetic linkage studies.

Another potential application of this procedure is the localization of mutations that are selected on the basis of a phenotype. In many genetic systems large numbers of mutants are available for study, but the mutations have not been precisely mapped. The inventive method allows rapid localization of many mutations to small DNA fragments that can be detected as single base substitutions. To increase the percentage of mismatches detected this method may readily be combined with physical analytical methods such as denaturing gradient gel electrophoresis (Myers et al. (1985), *Nuc. Acids Res* 13, 3131). These two methods complement each other since the basis of detection of mismatches in each differs markedly.

Methods of the invention can also be used to make a rapid determination of whether prospective parents carry lesions in the same gene and can thus serve as a method of determining the risk of a birth defect in the offspring. Perinatal screening, or screening of an embryo in vitro can also be performed. Other applications include forensics and paternity testing, in which methods of the invention can replace or complement RFLP mapping. The methods are also useful for the identification of useful traits in commercial (for example, agricultural) species. The simple, rapid, and sensitive nature of the claimed methods and their ability to be readily automated renders them practical for large scale screening of many samples or for screening a particular sample against a number of reference nucleic acids.

The invention is also useful for detecting mutations introduced during experimental manipulations (e.g., transformation, mutagenesis, PCR amplification, or after prolonged storage or freeze:thaw cycles). The method is therefore useful for testing genetic constructs that express therapeutic proteins or that are introduced into a patient for gene therapy purposes.

The method may also be used for rapid typing of bacterial and viral strains. By "type" is meant to characterize an isogeneic bacterial or viral strain by detecting one or more nucleic acid mutations that distinguishes the particular strain from other strains of the same or related bacteria or virus. As an example, genetic variation of the human immunodeficiency virus has led to the isolation of distinct HIV types, each bearing distinguishing gene mutations (Lopez-Galindez et al.(1991), *Proc. Natl. Acad. Sci. USA* 88, 4280). Other examples of test DNAs of particular interest for typing include test DNAs isolated from viruses of the family Retroviridae, for example, the human T-lymphocyte viruses or human immunodeficiency viruses (in particular any one of HTLV-I, HTLV-II, HIV-1, or HIV-2), DNA viruses of the family Adenoviridae, Papovaviridae, or Herpetoviridae, bacteria, or other organisms, for example, organisms of the order Spirochaetales, of the genus *Treponema* or *Borrelia*, of the order Kinetoplastida, of the species *Trypanosoma cruzi*, of the order Actinomycetales, of the family Mycobacteriaceae, of the species *Mycobacterium tuberculosis*, or of the genus *Streptococcus*.

Individuals skilled in the art will readily recognize that the compositions of the present invention can be assembled into a kit for the detection of mismatches. Typically, such a kit will include one of more of the following components: a Mu-end nucleic acid (e.g., a DNA), a phage Mu transposase, and means for determining if the Mu-end nucleic acid transposes into the target at a predominant site, and/or instructions for using the materials of the kit to test a subject or sample for the presence of a mismatch. In a preferred embodiment, the kit comprises a pre-assembled mixture of a Mu-end nucleic acid (e.g., a DNA) and a phage Mu transposase. Preferably, the kit will include a purified phage Mu transposase, either lyophilized or in a suitable buffer, and/or a purified Mu-end nucleic acid, either lyophilized or in a suitable buffer.

Optionally, the kit will also contain means for labeling the Mu-end nucleic acid; means for detecting the transposition products; one or more reaction mixtures suitable for use in the methods of the invention; and/or a pre-cast gel suitable for analyzing the transposition products. Alternatively, the kit may contain pre-labeled, or unlabeled Mu-end DNA already assembled with Mu transposase in an appropriate buffer, aliquoted in individual reaction tubes and frozen, so that the users can simply add their test target DNA preparations to the tubes to carry out the transposition reaction.

Also optionally, for example when the kit is designed to detect a particular mutation of interest, it may also include (optionally labeled) reference (control, wild type) DNA, and/or (optionally labeled) primers for PCR amplification of the portion of the gene suspected of containing the mutation. In preferred embodiments the kit will include: a first primer, and a second primer, the first and second primers defining a region which includes a potential mismatch site in a preselected gene; a control DNA, a first primer, and a second primer, the first and second primers defining a region which includes potential mismatch site in a preselected gene and wherein the control DNA is wild-type for the nucleotide(s) in the region of potential mismatch. The kit may also include pre-formed heteroduplexes with which to standardize reaction conditions and/or appropriate buffers (for example, enzyme dilution buffers or enzyme reaction buffers).

Another embodiment of the invention is an in vitro reaction mixture comprising a Mu-end nucleic acid, a phage Mu transposase, and a double strand target DNA comprising a mismatch.

In the foregoing and in the following examples, all temperatures are set forth in uncorrected degrees Celsius; and, unless otherwise indicated, all parts and percentages are by weight.

EXAMPLES

Example I

Materials and Methods

A. Proteins and DNA

MuA 77-663 was purified essentially as described (Baker et al. (1993), *Cell* 74, 723-33). λ DNA was purchased from Life Technologies. Rsa I was from New England Biolabs. λ DNA digested by Rsa I was purified by phenol-chloroform extraction and was resuspended in TE buffer. The oligonucleotides were synthesized at HHMI/Keck Oligonucleotide Synthesis Facility (Yale Univ.) and purified by electrophoresis on a urea-polyacrylamide gel (6). When indicated, oligo DNA was labeled on the 5'-end with T4 polynucleotide kinase (Pharmacia) and [γ-$^{32}$P]ATP (New England Nuclear). The Mu end DNA fragment was prepared by annealing the two oligonucleotides, MM1138 (5'-TCGGATGAAGCGGCGCACGAAAAACGC-GAAAGCGTTTCACGATAAATGCGAAAACA-3') (SEQ ID NO: 1) and MM1141 (5'-TGTTTTCGCATTTATCGTGAAACGCTTTCGCGTTTTTCGTGCGCCGCTTCA -3') (SEQ ID NO: 2). The regular target DNA fragment was prepared by annealing the two oligonucleotides, MM1063 (5'-CGTTCATTAGCACAATCACAGAAGACTA-GAATACAACCGCACATAAGATCAGAAGT-TAACTAGCACTAGTACTTGC-3') (SEQ ID NO: 3) and MM1064 (5'-GCAAGTACTAGTGCTAGTTAACTTCT-GATCTTATGTGCGGTTGTATTCTAGTCT-TCTGTGATTGTGCTAATGAACG-3') (SEQ ID NO: 4). The heteroduplex target DNA fragments have the same sequence as the homoduplex target DNA except for the mismatched nucleotides which are shown in the figures. Human DNA samples were obtained from Coriell Cell Repositories (Camden, N.J., USA). The patient DNA is NA11496, the sibling DNA is NA11497, and the normal DNA is NA14511. The primers for amplifying the CFTR gene were MM1482 (5'-TGGTAATAGGACATCTCCAAG-3') (SEQ ID NO: 5) and MM1483 (5'-ACCTTGCTAAAGAAATTCTTGC-3') (SEQ ID NO: 6). The child's DNA is NA14689, the mother's DNA is NA14690, and the father's DNA is NA14691. The primers for amplifying the DPα gene were MM1461 (5'-CGCGGATCCTGTGTCAACTTATGC-CGC-3') (SEQ ID NO: 7) and MM1462 (5'-GTGGCTG-CAGTGTGGTTGGAACGC-3') (SEQ ID NO: 8). The PCR reaction was performed using 0.3 μg DNA, 0.4 μM primers, 0.2 mM dNTPs and 2.5 U of PfuTurbo® hotstart DNA polymerase (Stratagene) per 50 μl reaction. The PCR was run for 35 cycles of 95° C. for 30 s, 55° C. for 30 s and 72° C. for 1 min in a Perkin Elmer Gene Amp system 9700. The amplified DNA was purified by a spin column (QIAquick PCR purification kit, Qiagen). The concentration of the amplified DNA was around 200 ng/μl. CHAPS and DMSO were from SIGMA.

B. Transposition Reactions

The reactions (15 μl) for FIG. 1 contained 150 nM Mu end DNA fragment, 75 nM target DNA fragment, 400 nM MuA77-663, 25 mM Hepes (pH 7.6), 15% (v/v) glycerol, 15% DMSO, 10 mM CHAPS, 10 mM MgCl$_2$ and 156 mM NaCl. The reactions (10 μl) for FIG. 2-3 contained 100 nM Mu DNA fragment, 100 nM target DNA fragment for FIG. 2, or specified amount of target DNA fragment (see legend to FIG. 3), 350 nM MuA77-663, 25 mM Hepes (pH 7.6), 15% (v/v) glycerol, 10% DMSO, 10 mM CHAPS, 10 mM MgCl$_2$ and 280 mM NaCl. Reactions were carried out at 30° C. for 30 min. For the experiments in FIG. 4-5, transpososomes were preformed in reaction mixture containing 100 nM labeled Mu DNA fragment, 400 nM MuA77-663, 25 mM Hepes (pH 7.6), 15% (v/v) glycerol, 15% DMSO, 10 mM CHAPS, and 156 mM NaCl. Reactions were carried out at 30° C. for 30 min. Then the reaction mixture was split into aliquots and the target DNA and MgCl$_2$ was added. The final reaction mixture contained 20 nM labeled Mu DNA fragment, 1.3 μl of the amplified DNA (about 260 ng) as a target DNA, 80 nM MuA77-663, 25 mM Hepes (pH 7.6), 15% (v/v) glycerol, 10% DMSO, 10 mM CHAPS, 10 mM MgCl$_2$ and 300 mM NaCl. Reactions were carried out at 30° C. for 5 min.

The reaction products were recovered by phenol-chloroform extraction and ethanol precipitation. About 1/10 of recovered DNA were used for analysis by 6% urea-polyacrylamide gel electrophoresis (6). The radioactivity was visualized by autoradiography using a Fuji BAS 2000 phosphorImager. Quantification of the bands was performed using Image Gauge V3.0 (Fuji Photo Film, Inc).

Example II

Mu Targets Mismatch DNA

We examined the effects of DNA distortion on Mu transposition target recognition by testing the ability of short DNA fragments that contained mismatch base pairs to function as transposition targets. We used the simplified in vitro reaction conditions with a pre-cleaved form of Mu end DNA fragment containing two transposase binding sites. The Mu end DNA was labeled at the 5'-end of the 51-nucleotide pre-cleaved strand that is to be joined to the target DNA (FIG. 1A-a). When 76 bp DNA without a mismatch (FIG. 1A-b) was used as the target, the length of the resulting recombinant fragments was randomly distributed from 68 bp to 115 bp (FIG. 1B, lane 2). This indicated that the Mu DNA was transferred to sites throughout the target DNA, except at the 5'-terminal 12 nt and 3'-terminal 17 nt. When the target DNA contained a mismatch, insertions to the normal duplex sites were suppressed and nearly 90% of the strand transfer products were either 91 nt- or 92 nt-long (FIG. 1B, lane 3). The observed size of the reaction products matched that of the two fragments that would result from Mu insertion with the mismatch located at the center of the 5-nucleotide target sequence (see FIG. 1D). To confirm this, the target DNA was labeled at the 5'-end of either strand and the size of the resulting products was examined. When non-mismatch DNA was used, the size of the DNA fragment released by formation of the recombinant strand was distributed from 12 nt to 60 nt without strong preference (FIG. 1C, lane 1, 2). When mismatch DNA was used, this released product was mainly found at 35 nt when the top strand as drawn in FIG. 1A-c was labeled (FIG. 1C, lane 3) and 36 nt when the bottom strand was labeled (FIG. 1C, lane 4). Taken together, we conclude that the preferential strand transfer to the mismatch-containing DNA occurred with the mismatch nucleotide at the center of the target sequence (FIG. 1D).

Figure 2A:
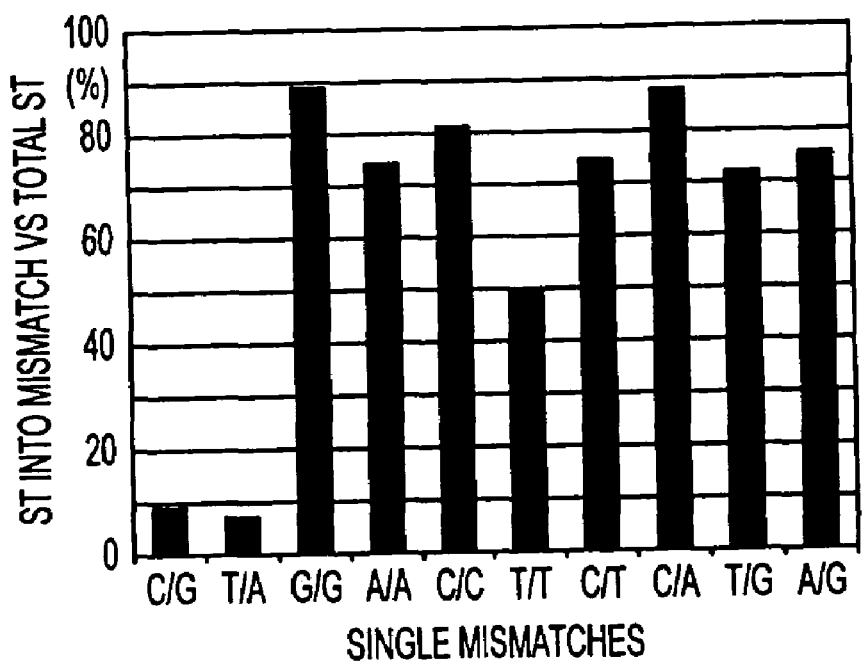
FIGS. 2A-2B show the efficiency of various mismatch targets.
Figure 2B:
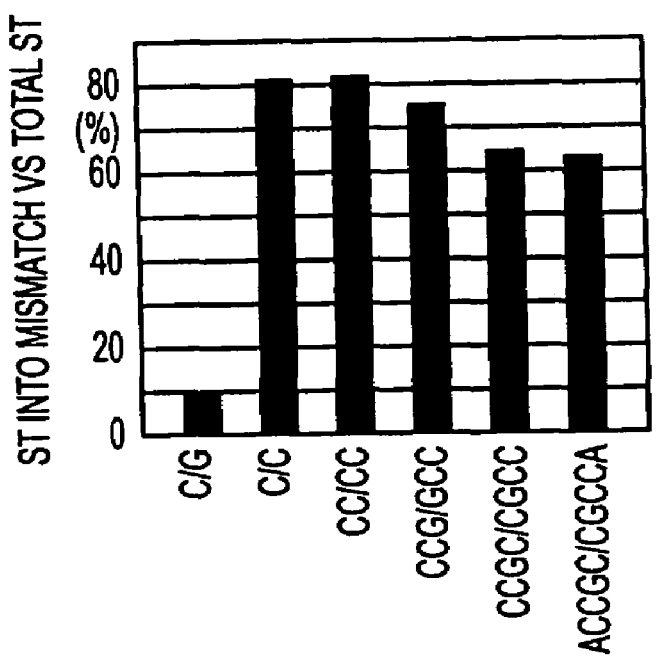

All 8 types of mismatched base pairs were efficiently used as target (FIG. 2A). A T/T mismatch, which was somewhat less strongly preferred compared to others, was still highly preferred over non-mismatch sites. We also examined targets having multiple nucleotide mismatches (bubbles) up to 5 nucleotides (FIG. 2B). Dinucleotide mismatches were utilized as well as single mismatches. Larger bubbles were also preferentially targeted, although the efficiency of targeting did not improve with the bubble size. The exact target locations were clustered around the bubble. Not all unusual DNA structures were strongly preferred as a transposition target. When the target DNA contained a single-nucleotide bulge as opposed to a mismatch, the bulge sites were not used as preferred targets, except for a moderate preference for a G- or A-bulge site. Instead, a weak insertion preference approximately one helical turn away from the bulge resulted in the products of 80 nt, 81 nt, 102 nt, and 103 nt (FIG. 1B, lane 4-7). Larger bulge sites were not preferred (FIG. 1B, lane8-10).

Figure 3:
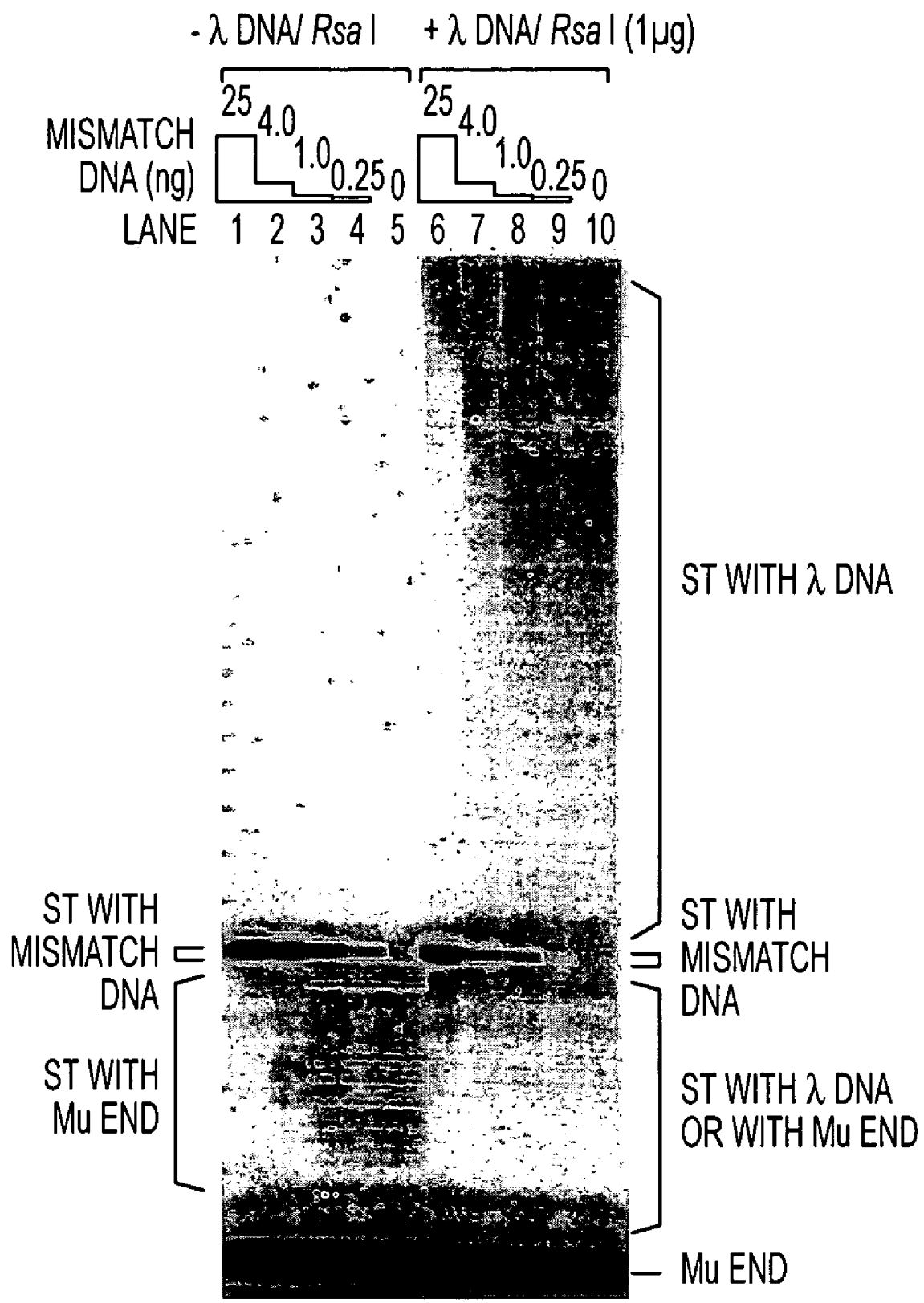
FIG. 3 shows the detection of mismatch DNA in the presence of a large excess of non-mismatch DNA. Target DNA was titrated from 25 ng to 0.25 ng in the absence or presence of 1 μg of λ DNA digested by Rsa I.

Because Mu transposase specifically targets mismatched nucleotides during recombination in vitro it may be useful for detection and mapping of mutations. To evaluate the usefulness of Mu transposition as a general mutation detection method, we needed to know the selectivity for a mismatched target site in the presence of a large excess of duplex target sites of heterogeneous sequence. To investigate the limit of detection of a mismatch site by selective Mu transposition, mismatched DNA target was titrated in the presence and absence of an excess amount of λ DNA as a non-mismatch random DNA. In the absence of the λ DNA, decreasing the amount of mismatch DNA caused an increase in use of the Mu-end DNA itself as a target, although the products that used the mismatch site were still clearly detectable (FIG. 3, lane 1-5). Addition of λ DNA caused only a modest decrease in the mismatch-targeted events (FIG. 3, lane 6-10). Transposition to a mismatched site on a 76 nt fragment could be detected in the presence of a 300,000 fold excess of non-mismatch sites (FIG. 3, lane 9).

Example III

Detection of Genomic Variations by Mu Transposition

A. Known Mutations

Figure 4A:
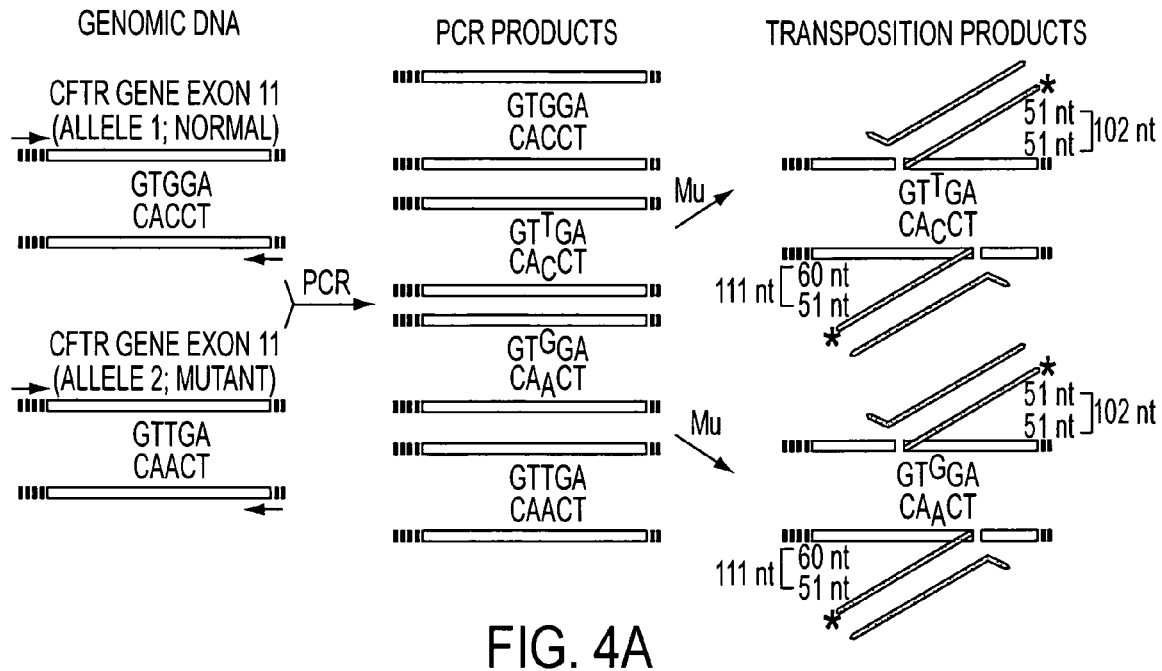
FIGS. 4A-4B show the detection of homozygous and heterozygous mutations in the CFTR gene by the method of the invention.
Figure 4B:
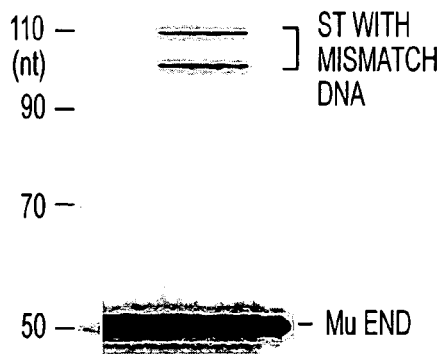

Next we tested genomic DNA from a cystic fibrosis (CF) patient who has a homozygous mutation in CFTR gene and her sibling who has heterozygous mutation to see whether the mutation was detectable by Mu transposition. Exon 11 of the CFTR gene was amplified by PCR using genomic DNA from a normal individual (N/N), the sibling (N/M), and the patient (M/M) as templates. Only when the sample DNA contained both the wild type and mutant sequence, will mismatch DNA be generated by denaturing-annealing steps during PCR (FIG. 4A). When the normal or the patient DNA was amplified and used as the target, no dominant strand transfer product was detected (FIG. 4B, lane 1-2). When the sibling DNA was used, the dominant strand transfer products were found at the 102 nt and 111 nt positions (FIG. 4B, lane 3), revealing that, as expected, mismatch DNA was generated during PCR and that strand transfer targeted this mismatch. When the amplified DNA from the mixture of normal and patient DNA was used, the dominant strand transfer products were found at the same positions as expected (FIG. 4B, lane 4). Homozygous mutations can be distinguished from heterozygous mutations by the requirement for co-amplification with the non-mutant sequence. Similar experiments using a mutant k-ras gene demonstrated the general applicability of this method for polymorphism detection and mapping.

B. Unknown Mutations

Figure 5:
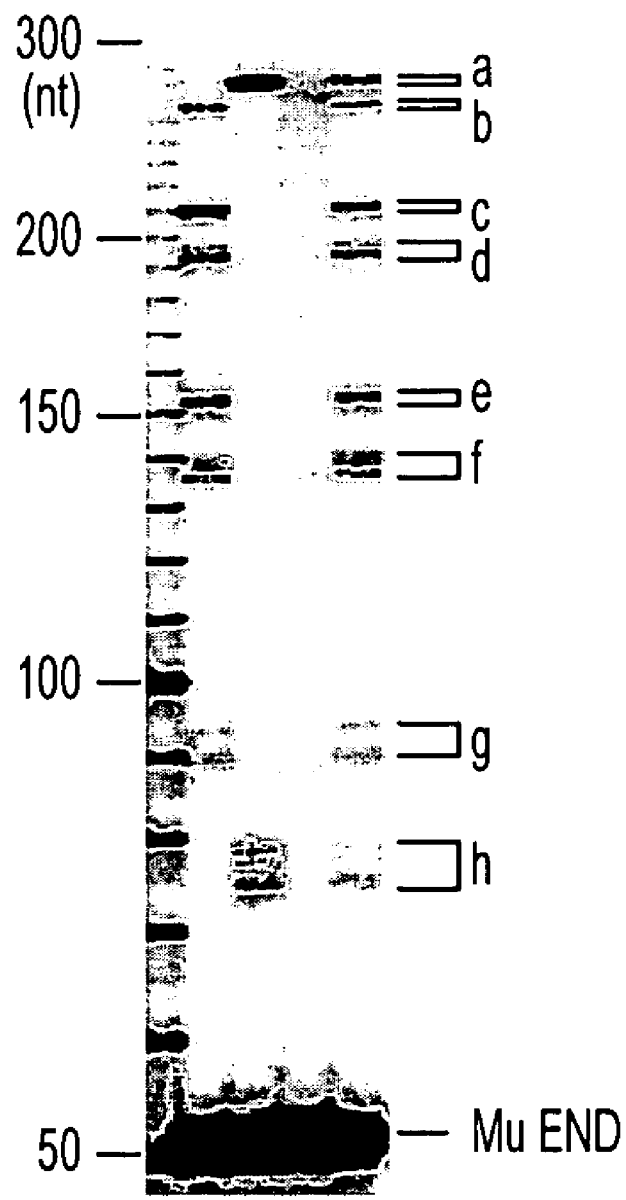
FIG. 5 shows the detection of a polymorphism in HLA region by the method of the invention. DPα gene in HLA region was amplified and the preferred transposition sites were compared between the family members. The template DNA used for PCR are indicated at the top. a-h indicate distinct ST products.

To investigate the capability of detection of unknown mutations, HLA (human leukocyte antigen) region, which is known to be highly polymorphic, was tested. DPα, one of the genes in HLA region, was amplified and the preferred transposition sites were compared between the family members. Each family member (child, mother, and father) exhibited a distinct pattern, showing that they have different heterozygous polymorphisms in the DPα gene (FIG. 5, lane 1-3). When DNA amplified from both mother's and father's DNA was used as the target, bands specific to the child (FIG. 5, from *a* to *g*) were evident as well as bands specific to the mother (FIG. 5, *a* and *h*). This result shows that the preferable sites in child's DNA are actually mismatch sites which arise from multiallelic differences between the parents and that this method can reliably detect multiple mismatches simultaneously.

From the foregoing description, one skilled in the art can easily ascertain the essential characteristics of this invention, and without departing from the spirit and scope thereof, can make changes and modifications of the invention to adapt it to various usage and conditions.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications, cited above and in the figures are hereby incorporated by reference.

We claim:

1. A method for detecting a mismatch in a test double stranded nucleic acid target, comprising
   a) contacting the target with
      i) a Mu-end nucleic acid, and
      ii) a phage Mu transposase,
   under conditions effective for the Mu-end nucleic acid to transpose predominantly into the target at about the site of a mismatch, and
   b) detecting transposition of the Mu-end nucleic acid into the target at a predominant site, indicating the presence of a mismatch at about that site.

2. The method of claim 1, wherein the Mu-end nucleic acid is detectable.

3. The method of claim 2, wherein the Mu-end nucleic acid is detectably labeled.

4. The method of claim 1, wherein the target nucleic acid is detectably labeled.

5. The method of claim 1, wherein the target and/or the Mu-end nucleic acid are DNA.

6. The method of claim 1, wherein the target is generated by PCR.

7. The method of claim 1, further comprising
   c) contacting a control duplex nucleic acid, comparable to the test double stranded nucleic acid target, but known to be free from mismatches, with
      i) a Mu-end nucleic acid, and
      ii) a phage Mu transposase,
   under conditions effective for the Mu-end nucleic acid to transpose into the control duplex at about the site of a mismatch,
   d) detecting transposition of the Mu-end DNA into the control duplex, and
   e) comparing the transposition of the Mu-end nucleic acid into the test target and into the control duplex,
   wherein an increased of transposition of the Mu-end nucleic acid into the test target at a predominant site compared to transposition of the Mu-end nucleic acid into the control duplex indicates the presence of a mismatch at that site in the test target.

8. The method of claim 7, wherein the detection and comparing comprise
   i) separating by size the products of the transposition reactions and
   ii) comparing the amount and sizes of the products from the treated test target with the products from the treated control duplex.

9. The method of claim 1, wherein the mismatch indicates the presence of a mutation.

10. The method of claim 1, wherein the mismatch indicates the presence of a polymorphism.

11. The method of claim 1, which is a method for typing a pathogenic microorganism strain.

12. The method of claim 1, which is a high throughput method.

13. The method of claim 1, which further comprises determining the location of the mismatch,
   wherein the transposition comprises nicking one strand of the target at about the site of the mismatch and ligating the 3' terminus of the proximal end of the Mu-end nucleic acid to the 5' terminus of the nicked target strand, thereby generating four transposition targets,
   further comprising determining the length of one or more of the transposition products,
   wherein the length of one or more of the transposition products indicates the site of the mismatch.

14. A method for detecting the presence of a mutation or polymorphism in a nucleic acid of interest, comprising
   a) generating a double stranded nucleic acid target having a first strand and a second strand, wherein the first strand comprises a portion of the nucleic acid of interest, which contains the mutation or polymorphism, and the second strand comprises a comparable portion of a wild type nucleic acid,
   b) contacting the double stranded nucleic acid target with
      i) a Mu-end nucleic acid, and
      ii) a phage Mu transposase,
   under conditions effective for the Mu-end nucleic acid to transpose predominantly into the target at about the site of a mismatch, and
   c) detecting transposition of the Mu-end DNA into the target at a predominant site, indicating the presence of a mutation or a polymorphism in the nucleic acid of interest.

15. The method of claim 14, wherein the nucleic acid of interest comprises a mutation which is diagnostic of a disease or a condition, or a susceptibility to the disease or condition.

16. The method of claim 14, wherein the nucleic acid of interest comprises a polymorphism.

17. The method of claim 14, wherein the nucleic acid of interest comprises a mutation that is in an essential gene.

18. The method of claim 14, wherein the nucleic acid of interest comprises a mutation in a CFTR, APC, p53, Rb, BRCA1, HMSH1, or HMLH1 gene.

19. The method of claim 14, which is a method for screening an embryo for the presence of a mutation.

20. The method of claim 14, which is a method for detecting the presence of a known mutation in a gene of interest.

21. The method of claim 14, which is a method for detecting the presence of a previously unidentified mutation in a gene of interest.

22. The method of claim 14, which is a method for diagnosing the presence or absence of a tumor-promoting mutation.

23. The method of claim 14, which further comprises determining the location of the mutation or polymorphism in the nucleic acid of interest,
   wherein the transposition comprises nicking one strand of the target at about the site of the mismatch and ligating the 3' terminus of the proximal end of the Mu-end nucleic acid to the 5' terminus of the nicked target strand, thereby generating four transposition targets,
   further comprising determining the length of one or more of the transposition products,
   wherein the length of one or more of the transposition products indicates the site of the mismatch.

24. The method of claim 23, wherein the determining of the length of the transposition products is achieved by separating the transposition products by size.

25. The method of claim 24, wherein the size separation is performed by electrophoresis.

26. The method of claim 25, wherein herein the electrophoresis is on an acrylamide gel, an agarose gel, or in a capillary tube.

27. The method of claim 23, further wherein, following step b), the product(s) of the transposition reaction are amplified using one Mu end specific primer and one primer specific to a region of interest from the target nucleic acid.

28. A method of detecting the presence and location of a mutation or polymorphism in a DNA of interest, comprising a) amplifying by PCR a portion of the DNA of interest suspected of containing the mutation or polymorphism and, optionally, co-amplifying the same portion of a comparable control DNA which lacks any mutation or polymorphism within that portion, to form a duplex,
b) contacting the duplex with
   i) a Mu-end nucleic acid, and
   ii) a phage Mu transposase,
under conditions effective for the Mu-end nucleic acid to transpose predominantly into the duplex at about the site of a mismatch resulting from the mutation or polymorphism,
c) separating by size the products of the transposition reaction, and
d) determining the amount and size of the transposition product(s),
wherein transposition of the Mu-end nucleic acid into the duplex at a predominant site indicates the presence of a mutation or polymorphism in the nucleic acid of interest, and
wherein the size of the transposition product(s) indicates the site of the mutation or polymorphism, and
wherein the presence of a predominant site of Mu-end DNA integration when the DNA of interest is subjected to PCR in the absence of the control DNA indicates that the DNA of interest is heterozygous for the mutation or polymorphism, and
wherein the presence of a predominant site of Mu-end DNA integration only when the DNA of interest is co-amplified by PCR in the presence of the control DNA indicates that the DNA of interest is homozygous for the mutation or polymorphism.

29. The method of claim 28, wherein the size separation is performed by electrophoresis.

30. The method of claim 29, wherein herein the electrophoresis is on an acrylamide gel, an agarose gel, or in a capillary tube.

31. The method of claim 28, further wherein, following step b), the product(s) of the transposition reaction are amplified using one Mu end specific primer and one primer specific to a region of interest from the target nucleic acid.

* * * * *